US007387782B2

(12) United States Patent
Zaia et al.

(10) Patent No.: US 7,387,782 B2
(45) Date of Patent: Jun. 17, 2008

(54) PROTEIN KINASE DEFICIENT, IMMUNOLOGICALLY ACTIVE CMVPP65 MUTANTS

(75) Inventors: John A. Zaia, Arcadia, CA (US); Ghislaine Hawkins, Glendora, CA (US)

(73) Assignee: City of Hope, Duarte, CA (US)

( * ) Notice: Subject to any disclaimer, the term of this patent is extended or adjusted under 35 U.S.C. 154(b) by 272 days.

(21) Appl. No.: 11/206,162

(22) Filed: Aug. 18, 2005

(65) Prior Publication Data
US 2006/0018929 A1    Jan. 26, 2006

Related U.S. Application Data

(62) Division of application No. 10/409,063, filed on Apr. 9, 2003, now Pat. No. 7,025,969, which is a division of application No. 09/815,330, filed on Mar. 23, 2001, now Pat. No. 6,835,383.

(60) Provisional application No. 60/191,464, filed on Mar. 23, 2000.

(51) Int. Cl.
*A61K 39/245* (2006.01)

(52) U.S. Cl. ............................... 424/230.1; 424/186.1; 435/6

(58) Field of Classification Search ............. 424/230.1, 424/186.1; 435/6
See application file for complete search history.

(56) References Cited

U.S. PATENT DOCUMENTS

| | | | |
|---|---|---|---|
| 3,959,466 A | 5/1976 | Plotkin | |
| 4,058,598 A | 11/1977 | Stern et al. | |
| 4,689,225 A | 8/1987 | Pereira | |
| 4,716,104 A | 12/1987 | Harris et al. | |
| 4,762,780 A | 8/1988 | Spector et al. | |
| 5,075,213 A | 12/1991 | Pande et al. | |
| 5,180,813 A | 1/1993 | Stinski | |
| 5,248,768 A | 9/1993 | Lussenhop et al. | |
| 6,074,645 A | 6/2000 | Diamond et al. | |
| 6,156,317 A | 12/2000 | Diamond et al. | |

OTHER PUBLICATIONS

Pande, H., et al., "Structural Analysis of a 64-kDa Major Structural Protein of Human Cytomegalovirus (Towne): Identification of a Phosphorylation Site and Comparison to pp65 of HCMV (AD169)," *Virology*, vol. 178, pp. 6-14, 1980.
Meyers, J.D., et al., "Risk Factors for Cytomegalovirus Infection After Human Marrow Transplantation," *The Journal of Infectious Diseases*, vol. 153, No. 3, pp. 478-488, Mar. 1986.
Quinnan, G.V., Jr., et al., "Cytotoxic T Cells in Cytomegalovirus Infection; HLA-Restricted T-Lymphocyte and Non-T-Lymphocyte Cytotoxic Responses Correlate with Recovery from Cytomegalovirus Infection in Bone-Marrow-Transplant Recipients," *The New England Journal of Medicine*, vol. 307, No. 1, Jul. 1, 1982, pp. 7-13.
Pande, H., et al., Human Cytomegalovirus Strain Towne pp65 Gene: Nucleotide Sequence and Expression in *Escherichia coli*, *Virology*, vol. 182, pp. 220-228, 1991.
McLaughlin-Taylor, E., et al., "Identification of the Major Late Human Cytomegalovirus Matrix Protein pp65 as a Target Antigen for CD8+ Virus-Specific Cytotoxic T Lymphocytes," *Journal of Medical Virology*, vol. 43, pp. 103-110, 1994.
Walter, E.A., et al., "Reconstitution of Cellular Immunity Against Cytomegalovirus in Recipients of Allogeneic Bone Marrow by Transfer of T-Cell Clones from the Donor," *The New England Journal of Medicine*, pp. 1038-1044, Oct. 19, 1995, vol. 333, No. 16.
Borysiewicz, L.K., et al., "Human cytomegalovirus-specific cytotoxic T lymphocytes: requirements for in vitro generation and specificity," *Eur. J. Immunol.*, vol. 13, pp. 804-809, 1983.
Zhou, Y.F., et al., "Association Between Prior Cytomegalovirus Infection and the Risk of Restinosis After Coronary Atherectomy," *The New England Journal of Medicine*, pp. 624-630 Aug. 29, 1996.
Speir, Edith, et al., "Potential Role of Human Cytomegalovirus and p53 Interaction in Coronary Restinosis," *Science*, vol. 265, pp. 391-394, Jul. 15, 1994.
Li, C.-R., et al., "Recovery of HLA-Restricted Cytomegalovirus (CMV)-Specific T-Cell Responses After Allogeneic Bone Marrow Transplant: Correlation with CMV Disease and Effect of Ganciclovir Prophylaxis," *Blood*, vol. 83, No. 7, pp. 1971-1979, Apr. 1, 1994.
Goodrich, J.M., et al., "Early Treatment with Ganciclovir to Prevent Cytomegalovirus Disease After Allogeneic Bone Marrow Transplantation," *The New England Journal of Medicine*, vol. 325, No. 23, pp. 1601-1607, Dec. 5, 1991.
Reusser, P., et al., "Cytotoxic T-Lymphocyte Response to Cytomegalovirus After Human Allogeneic Bone Marrow Transplantation: Pattern of Recovery and Correlation With Cytomegalovirus Infection and Disease," *Blood*, vol. 78, No. 5, pp. 1373-1380, Sep. 1, 1991.
Wills, M.R., et al., "The Human Cytotoxic T-Lymphocyte (CTL) Response to Cytomegalovirus Is Dominated by Structural Protein pp65: Frequency, Specificity, and T-Cell Receptor Usage of pp65-Specific CTL," *Journal of Virology*, pp. 7569-7579, Nov. 1996.
Gilbert, M.J., et al., "Selective Interference with Class I major Histocompatability Complex Presentation of the Major Immediate-Early Protein following Infection with Human Cytomegalovirus," *Journal of Virology*, pp. 3461-3469, Jun. 1993, vol. 67, No. 6.
Goodrich, J.M., et al., "Ganciclovir Prophylaxis To Prevent Cytomegalovirus Disease After Allogeneic Marrow Transplant," *Annals of Internal Medicine*, vol. 118, pp. 173-178, 1993.

(Continued)

*Primary Examiner*—Ali R. Salimi
(74) *Attorney, Agent, or Firm*—Rothwell, Figg, Ernst & Manbeck, P.C.

(57) ABSTRACT

This invention relates to mutated CMVpp65, a viral structural protein which activates cell mediated immunity in humans infected with CMV. The mutations remove undesirable protein kinase activity naturally present in the protein and make it suitable for the production of both DNA and protein vaccines. Therefore, the invention provides proteins and DNAS, as well as vaccines comprising the proteins and DNAs, including cellular vaccines and vectors. Other embodiments of the invention relate to methods of enhancing immune response and vaccinating against CMV, including gene therapy methods and vectors.

7 Claims, 7 Drawing Sheets

OTHER PUBLICATIONS

Schmidt, G.M., et al., "A Randomized, Controlled Trial of Prophylactic Ganciclovir for Cytomegalovirus Pulmonary Infection in Recipients of Allogeneic Bone Marrow Transplants," *The New England Journal of Medicine*, vol. 324, No. 15, pp. 1005-1011, Apr. 11, 1991.

Rasmussen, L., "Immune Response to Human Cytomegalovirus Infection," *Current Topics in Microbiology and Immunology*, vol. 154, pp. 221-255, 1990.

Forman, S.J., et al., "A 64,000 Dalton Matrix Protein of Human Cytomegalovirus Induces in Vitro Immune Responses Similar to Those of Whole Viral Antigen," *The Journal of Immunology*, vol. 134, No. 5, pp. 3391-3395, May 1985.

Borysiewicz, L.K., et al., "Human Cytomegalovirus-Specific Cytotoxic T Cells—Relative Frequency of Stage-specific CTL Recognizing the 72kD Immediate Early Protein and Glycoprotein B Expressed by Recombinant Vaccinia Viruses," *J. Exp. Med.*, vol. 168, pp. 919-931, Sep. 1988.

Diamond, D.J., et al., "Development of A Candidate HLA A*0201 Restricted Peptide-Based Vaccine Against Human Cytomegalovirus Infection," *Blood*, vol. 90, No. 5, pp. 1751-1767, Sep. 1, 1997.

Winston, D.J., et al., "Ganciclovir Prophylaxis of Cytomegalovirus Infection and Disease in Allogeneic Bone Marrow Transplant Recipients—Results of a Placebo-Controlled, Double-Blind Trial," *Annals of Internal Medicine*, vol. 118, pp. 179-184, 1993.

Greenberg, P.D., et al., "Development of a Treatment Regimen for Human Cytomegalovirus (CMV) Infection in Bone Marrow Transplantation Recipients by Adoptive Transfer of Donor-Derived CMV-Specific T Cell Clones Expanded In Vitro," *Annals New York Academy of Sciences*, vol. 636, pp. 184-195, 1991.

Ohlin, M., et al., "Characterization of human monoclonal antibodies directed against the pp65-kD matrix antigen of human cytomegalovirus," *Clin. Exp. Immunol.*, vol. 84, pp. 508-514, 1991.

Rüger, B., et al., "Primary Structure and Transcription of the Genes Coding for the Two Virion Phosphoproteins pp65 and pp71 of Human Cytomegalovirus," *Journal of Virology*, pp. 446-453, Feb. 1987, vol. 61, No. 2.

Boppana, S.B., et al., "Recognition of Human Cytomegalovirus Gene Products by HCMV-Specific Cytotoxic T Cells," *Virology*, vol. 222, pp. 293-296, 1996.

Irmiere, A., et al., "Isolation and Characterization of a Noninfectious Virion-like Particle Released from Cells Infected with Human Strains of Cytomegalovirus," *Virology*, vol. 130, pp. 118-133, 1983.

Retière, C., et al., "Generation of Cytomegalovirus-Specific Human T-Lymphocyte Clones by Using Autologous B-Lymphoblastoid Cells with Stable Expression of pp65 or IE1 Proteins: a Tool To Study the Fine Specificity of the Antiviral Response," *Journal of Virology*, pp. 3948-3952, May 2000, vol. 74, No. 9.

Kern, Fl., et al., "Target Structures of the CD8+-T-Cell Response to Human Cytomegalovirus: the 72-Kilodalton Major Immediate-Early Protein Revisited," *Journal of Virology*, pp. 8179-8184, Oct. 1999, vol. 73, No. 10.

Gyulai, Z., et al., "Cytotoxic T Lymphocyte (CTL) Responses to Human Cytomegalovirus pp65, IE1-Exon4, gB, pp150, and pp28 in Healthy Individuals: Reevaluation of Prevalence of IE1 Specific CTLs," *The Journal of Infectious Diseases*, vol. 181, pp. 1537-1546, 2000.

Periera. L., et al., "Monoclonal Antibodies to Human Cytomegalovirus: Three Surface Membrane Proteins with Unique Immunological and Electrophoretic Properties Specify Cross-Reactive Determinants," *Infection and Immunity*, pp. 924-932, Jun. 1982, vol. 36, No. 3.

Gibson, W., et al., "Selection of Particles and Proteins for Use as Human Cytomegalovirus Subunit Vaccines, in CMV: Pathogenesis and Prevention of Human Infection," March of Dimes Birth Defects Foundation, *Birth Defects: Original Article Series*, vol. 20, No. 1, pp. 305-324, 1984.

Gönczöl, E., et al., "Preclinical evaluation of an ALVAC (canarypox)-human cytomegalovirus glycoprotein B vaccine candidate," *Vaccine*, vol. 13, No. 12, 1995, pp. 1080-1085.

Khattab, B. A.-M., "Three T-Cell Epitopes Within the C-Terminal 265 Amino Acids of the Matrix Protein pp65 of Human Cytomegalovirus Recognized by Human Lymphocytes," *Journal of Medical Virology*, vol. 52, pp. 68-76, 1997.

Plotkin, S. A., et al., Vaccines for the Prevention of Human Cytomegalovirus Infection, Reviews of Infectious Diseases, vol. 12, Supplement 7, pp. S827-S838, Sep.-Oct. 1990.

Plotkin, S. A., et a., "Effect of Towne Live Virus Vaccine on Cytomegalovirus Disease after Renal Transplant," *Annals of Internal Medicine*, vol. 114, No. 7, pp. 525-531, Apr. 1, 1991.

Gibson, W., "Structural and Nonstructural Proteins of Strain Colburn Cytomegalovirus," *Virology*, vol. 111, pp. 516-537, 1981.

Plotkin, S. A., et al., "Protective Effects of Towne Cytomegalovirus Vaccine Against Low-Passage Cytomegalovirus Administered as a Challenge," The Journal of Infectious Diseases, vol. 159, No. 5, pp. 860-865, May 1989.

Gönczöl, E., et al., "Humoral Immune Response to Cytomegalovirus Towne Vaccine Strain and to Toledo Low-Passage Strain," *The Journal of Infectious Diseases*, vol. 159, No. 5, pp. 851-859, May 1989.

Pande, H., et al., "Genomic Localization of the Gene Encoding a 32-kDa Capsid Protein of Human Cytomegalovirus," *Virology*, vol. 167, pp. 306-310, 1988.

Stinski, M. F., et al., "Organization and Expression of the Immediate Early Genes of Human Cytomegalovirus," *Journal of Virology*, vol. 46, No. 1, pp. 1-14, Apr. 1983.

Roby, C., et al., "Characterization of Phosphoproteins and Protein Kinase Activity of Virions, Noninfectious Enveloped Particles, and Dense Bodies of Human Cytomegalovirus," *Journal of Virology*, vol. 59, No. 3, pp. 714-727, Sep. 1986.

DelVal, M., et al., "Protection against Lethal Cytomegalovirus Infection by a Recombinant Vaccine Containing a Single Nonameric T-Cell Epitope," *Journal of Virology*, vol. 65, No. 7, pp. 3641-3646, Jul. 1991.

Tamashiro, J. C., et al., "Construction of a Cloned Library of the *EcoRI* Fragments from the Human Cytomegalovirus Genome (Strain AD169)," *Journal of Virology*, vol. 42, No. 2, pp. 547-557, May 1982.

Clark, B. R., et al., "Isolation and Partial Chemical Characterization of a 64,000-Dalton Glycoprotein of Human Cytomegalovirus," *Journal of Virology*, vol. 49, No. 1, pp. 279-282, Jan. 1984.

Pande, H., et al., "Cloning and physical mapping of a gene fragment coding for a 64-kilodalton major late antigen of human cytomegalovirus," *Proc. Natl. Acad. Sci. USA*, vol. 81, pp. 4965-4969, Aug. 1984.

Riddell, S. R., et al., "Class I MHC-Restricted Cytotoxic T Lymphocyte Recognition of Cells Infected with Human Cytomegalovirus Does Not Require Endogenous Viral Gene Expression," *The Journal of Immunology*, vol. 146, No. 8, pp. 2795-2804, Apr. 15, 1991.

Spector, S. A., "Transmission of Cytomegalovirus Among Infants in Hospital Documented by Restriction-Endonuclease-Digestion Analyses," *The Lancet*, pp. 378-381, Feb. 19, 1983.

Kern, F., et al., "Analysis of CD8 T cell reactivity to cytomegalovirus using protein-spanning pools of overlapping pentadecapeptides," *Eur. J. Immunol.*, vol. 30, pp. 1676-1682, 2000.

Pachl, C., et al., "The Human Cytomegalovirus Strain Towne Glycoprotein H Gene Encodes Glycoprotein p86," *Virology*, vol. 169, pp. 418-426, 1989.

Spaete, R. R., et al., "Human Cytomegalovirus Strain Towne Glycoprotein B Is Processed by Proteolytic Cleavage," *Virology*, vol. 167, pp. 207-225, 1988.

Benmohamed, Lbachir et al., "Induction of CTL Response by a Minimal Epitope Vaccine in HLA A★0201/DR1 Transgenic Mice: Dependence on HLA Class II Restricted $T_H$ Response," *Hum. Immunol.* 61:764-79, 2000.

Beninga, J. et al., "Comparative Analysis of Fourteen Individual Human Cytomegalovirus Proteins for Helper T Cell Response,"*Journal of General Virology* 76:153-160, 1995.

Boppana, Suresh B. et al., "Recognition of Human Cytomegalovirus Gene Products by HCMV-Specific Cytotoxic T Cells," *Virology* 222, (Article No. 0424): 293-296, 1996.

Chee, M.S. et al., "Analysis of the Protein-Coding Content of the Sequence of Human Cytomegalovirus Strain AD169," *Current Topics in Microbiology and Immunology* 154: 125-169, 1990.

Grefte, J.M. et al., "Cytomegalovirus Antigenemia Assay: Identification of the Viral Antigen as the Lower Matrix Protein PP65," *The Journal of Infectious Diseases* 166: 683-4, 1992.

Lolli, Francesco et al., "T and B Cell Responses to Cytomegalovirus Antigens in Healthy Blood Donors and Bone Marrow Transplant Recipients," *FEMS Immunol. Med. Microbiol* 7: 55-62, 1993.

Michelson, S. et al., "Properties of a Human Cytomegalovirus-Induced Protein Kinase," *Virology* 134: 259-268, 1984.

Plotkin, Stanley A., "Cytomegalovirus Vaccine," *Am Heart J.* 138 (No. 5, Part 2): S484-S487, 1999.

Ohlin, Mata et al., "Human Antibody Reactivity Against the Lower Matrix Protein (pp65) Produced by Cytomegalovirus," *Clin. Diagn Lab. Immunol.* 2(3): 325-329, 1995.

Shirai, Mutsunori et al., "CTL Responses of HLA-A2.1-Transgenic Mice Specific for Hepatitis C Viral Peptides Predict Epitopes for CTL of Humans Carrying HLA-A2.1," *The Journal of Immunology* 154: 2733-2742, 1995.

Solache, Alejandra et al., "Identification of Three HLA-A★0201-Restricted Cytotoxic T Cell Epitopes in the Cytomegalovirus Protein pp65 That Are Conserved Between Eight Strains of the Virus," *The Journal of Immunology* 163: 5512-5518, 1999.

Somogyi, Teresa et al., "Genomic Location of a Human Cytomegalovirus Protein with Protein Kinase Activity (PK68)," *Virology* 174: 276-285, 1990.

Sun, Qi et al., "B Lymphoblastoid Cell Lines as Efficient APC to Elicit $CD8^+$ T Cell Responses Against a Cytomegalovirus Antigen[1]," *The Journal of Immunology* 165: 4105-4111, 2000.

Wentworth, Peggy A. et al., "Identification of A2-Restricted Hepatitis C Virus-Specific Cytotoxic T Lymphocyte Epitopes from Conserved Regions of the Viral Genome," *Int. Immunol.* 8 (5): 651-659, 1996.

Yao, Zhi-Qiang et al., "Site-Directed Mutation in a Conversed Kinase Domain of Human Cytomegalovirus-pp65 with Preservation of Cytotoxic T Lymphocyte Targeting," *Vaccine* 19: 1628-1635, 2001.

Zaia, John A. et al., "Infrequent Occurrence of Natural Mutations in the $pp65_{495-503}$: Epitope Sequence Presented by the HLA A*0201 Allele Among Human Cytomegalovirus Isolates," *J. Virol.* 75 (5): 2472-2474, 2001.

SEQUENCE LISTING

<160> NUMBER OF SEQ ID NOS: 12

<210> SEQ ID NO 1
<211> LENGTH: 6
<212> TYPE: PRT
<213> ORGANISM: Human cytomegalovirus
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid

<400> SEQUENCE: 1

Glu Xaa Glu Xaa Xaa Glu
1               5

<210> SEQ ID NO 2
<211> LENGTH: 27
<212> TYPE: DNA
<213> ORGANISM: Artificial Sequence
<220> FEATURE:
<223> OTHER INFORMATION: mutagenic primer for CMVpp65

<400> SEQUENCE: 2
gcgggccgca accgcaaatc agcatcc                                         27

<210> SEQ ID NO 3
<211> LENGTH: 27
<212> TYPE: DNA
<213> ORGANISM: Artificial Sequence
<220> FEATURE:
<223> OTHER INFORMATION: mutagenic primer for CMVpp65

<400> SEQUENCE: 3
ggatgctgat ttgcggttgc ggcccgc                                         27

<210> SEQ ID NO 4
<211> LENGTH: 36
<212> TYPE: DNA
<213> ORGANISM: Artificial Sequence
<220> FEATURE:
<223> OTHER INFORMATION: mutagenic primer for CMVpp65

<400> SEQUENCE: 4
gagtccaccg tcgcgcccaa agaggacacc gacgag                               36

<210> SEQ ID NO 5
<211> LENGTH: 36
<212> TYPE: DNA
<213> ORGANISM: Artificial Sequence
<220> FEATURE:
<223> OTHER INFORMATION: mutagenic primer for CMVpp65

<400> SEQUENCE: 5
ctcgtcggtg tcctctttgg gggcgacggt ggactc                               36

<210> SEQ ID NO 6
<211> LENGTH: 9
<212> TYPE: PRT

```
<213> ORGANISM: Human cytomegalovirus

<400> SEQUENCE: 6

Asn Leu Val Pro Met Val Ala Thr Val
1               5

<210> SEQ ID NO 7
<211> LENGTH: 24
<212> TYPE: DNA
<213> ORGANISM: Artificial Sequence
<220> FEATURE:
<223> OTHER INFORMATION: PCR primer for CMVpp65

<400> SEQUENCE: 7
gaattcacta gtgtaagtac cgcc                                          24

<210> SEQ ID NO 8
<211> LENGTH: 25
<212> TYPE: DNA
<213> ORGANISM: Artificial Sequence
<220> FEATURE:
<223> OTHER INFORMATION: PCR primer for CMVpp65

<400> SEQUENCE: 8
gactggatcc ctgcagaaaa gaccc                                         25

<210> SEQ ID NO 9
<211> LENGTH: 7
<212> TYPE: PRT
<213> ORGANISM: Human cytomegalovirus

<400> SEQUENCE: 9

Ala Gly Arg Lys Arg Lys Ser
1               5

<210> SEQ ID NO 10
<211> LENGTH: 19
<212> TYPE: PRT
<213> ORGANISM: Human cytomegalovirus

<400> SEQUENCE: 10

Ala Pro Glu Glu Asp Thr Asp Glu Asp Ser Asp Asn Glu Ile His Asn
1               5                   10                  15

Pro Ala Val

<210> SEQ ID NO 11
<211> LENGTH: 7
<212> TYPE: PRT
<213> ORGANISM: Artificial Sequence
<220> FEATURE:
<223> OTHER INFORMATION: Mutated PK domain II of CMVpp65

<400> SEQUENCE: 11

Ala Gly Arg Asn Arg Lys Ser
1               5

<210> SEQ ID NO 12
<211> LENGTH: 19
<212> TYPE: PRT
<213> ORGANISM: Artificial Sequence
<220> FEATURE:
<223> OTHER INFORMATION: Mutated PK domain VIII of CMVpp65
```

```
<400> SEQUENCE: 12

Ala Pro Lys Glu Asp Thr Asp Glu Asp Ser Asp Asn Glu Ile His Asn
1               5                   10                  15

Pro Ala Val
```

PROTEIN KINASE DEFICIENT, IMMUNOLOGICALLY ACTIVE CMVPP65 MUTANTS

CROSS-REFERENCE TO RELATED APPLICATIONS

This application is a divisional of prior application Ser. No. 10/409,063, filed Apr. 9, 2003, now U.S. Pat. No. 7,025,969, which is a divisional of application Ser. No. 09/815,330, filed Mar. 23, 2001, now U.S. Pat. No. 6,835,383, which claims priority from U.S. provisional application Ser. No. 60/191,464, filed Mar. 23, 2000.

STATEMENT REGARDING FEDERALLY SPONSORED RESEARCH

This invention was made with Government support in the form of Grant No. USPHS 30206, from the United States Department of Health and Human Services, National Institutes of Health. The United States Government may have certain rights in this invention.

BACKGROUND OF THE INVENTION

1. Technical Field

The present invention relates to mutants of the tegument protein of human cytomegalovirus (CMV) known as CMVpp65. The mutants desirably do not exhibit the protein kinase activity which is associated with the native pp65 protein but retain its desirable immunologic target characteristics.

2. Description of the Background Art

The CMV genome is relatively large (about 235k base pairs) and has the capacity to encode more than two hundred proteins. CMV is composed of a nuclear complex of double-stranded DNA surrounded by capsid proteins having structural or enzymatic functions, and an external glycopeptide- and glycolipid-containing membrane envelope. CMV is a member of the herpes virus family and has been associated with a number of clinical syndromes.

Human cytomegalovirus is not only a significant cause of morbidity in persons undergoing immunosuppressive therapy, but remains the major infectious cause of congenital malformations and mental retardation (26, 38, 53) (see the appended list of References for the identification of references cited throughout this specification). Although improved antiviral chemotherapy is becoming available for management of CMV infection, the large number of congenital infections (approximately 35,000 newborns per years in the U.S. (9)) underscores the need for an effective CMV vaccine (37), especially one which can be used safely in healthy persons. Attenuated and recombinant live virus vaccine approaches have been proposed, but safe use of these types of vaccines in healthy populations remains to be shown. Subunit vaccines are attractive because they have the potential to boost the immune system against certain viral proteins without risking viral infection or viral recombination.

CMV infection is widespread and persistent, and can become reactivated and clinically evident in the immunosuppressed patient. Because human cytomegalovirus is relatively common, yet is associated with extremely serious health conditions, a considerable effort has been made to study the biology of the virus with the aims of improving diagnosis of the disease as well as developing preventative and therapeutic strategies.

It would be highly desirable to deliver an effective vaccine derived from CMV that would impart immunity to persons at risk of CMV disease such as a bone marrow transplant (BMT) recipient, a solid organ recipient, a heart patient, an AIDS patient or a woman of child-bearing years. No such vaccine presently is commercially available, however.

Cell-mediated immunity (CMI) plays an essential role in recovery from acute CMV infection and in the control of persistent CMV infection. The generation of cytotoxic T lymphocytes (CTL) is a most important factor in limiting CMV disease. Several proteins encoded by CMV are known to be recognized by the cellular immune system and elicit CTL. Borysiewicz et al. (2) first described the role of specific CMV proteins in CTL induction. The non-virion, immediate early proteins of CMV (CMV-IE), as well as the envelope glycoprotein, CMVgB, activate CTL function, however, the internal matrix proteins of the virus, CMVpp65 and CMVpp150, are more prevalent immune targets. CMVpp65 is the immunodominant protein: 70-90% of all CMV-specific CTL recognize this protein.

CMVpp65 is not essential for virus replication, therefore it may function to facilitate host cell changes important to virus spread. CMVpp65 has emerged as the primary target of CMV-specific CTL. Because it is a structural virus protein, it is available as an immune target immediately after infection, in the absence of virus replication. Thus, CMVpp65 is a preferred target for the cellular immune system.

CMVpp65 is known to interact with the cellular polo-like kinase-1 that is present at high levels during cellular mitosis (15). It contains redundant nuclear localization signals (17, 43) and becomes associated with nuclear lamina and condensed chromosomes during infection (8, 42). Thus, CMVpp65 clearly has nuclear and chromosomal trafficking ability that could represent an unknown risk if the protein were expressed in normal cells.

CMVpp65 also has been reported to have endogenous serine/threonine phosphotransferase activity (2, 3, 31, 32, 35, 41), however, it lacks several of the recognizable protein kinase (PK) consensus domains (21) (see FIG. 1). The kinase activity of CMVpp65 remains incompletely understood, but certain consensus sequences conserved threonine/serine/tyrosine PK catalytic domain are found within the 173 amino acid carboxy-terminal region of CMVpp65 (45). Only three subdomains align properly with these conserved residues of the catalytic domain (21) but two other subdomains are present. These CMVpp65 motifs consist of the catalytic subdomain I (amino acids 422-427; EXEXXE; SEQ. ID NO: 1), subdomain II (amino acid 436; K), and subdomain VIB (amino acids 543-545; RDL. See FIG. 1. The sequences not in precise alignment are subdomain VIII (amino acids 463-465; APE, upstream from subdomain VIB and subdomain XI (carboxyl terminal amino acid 460; R).

PK activity plays an important role in the regulation of normal and transformed cell growth (7, 11, 25) and is important in viral regulation of cellular functions (29) and in regulation of virus transcription, DNA synthesis, and virion assembly (18, 36, 47, 51, 52). Because Protein kinases play an important role in the regulation of both normal and malignant cell growth (46), DNA vaccines (13, 34) that depend on the expression of intact CMVpp65 also could pose problems associated with introduction of PK activity into normal cells. The growth effects of increased kinase activity in healthy cells could limit the use of intact CMVpp65 as a vaccine, especially in children and women of child-bearing age. Therefore, new CMVpp65-derived sequences which could be used in DNA vaccines, yet which lack the undesired activities of the native protein would be highly useful.

SUMMARY OF THE INVENTION

Figure 1:
FIG. 1 is a diagram illustrating the protein kinase (PK) domains of CMVpp65, with expression vectors. Putative PK domains (Roman numerals), peptide sequences (upper case letters with mutated amino acid in bold type) and nucleotide sequences (lower case letters) for the targeted amino acids in domains II and VIII are shown. The expression plasmids, made in pQE9 vector under the control of CMV promoter (CMVp), are shown for the native CMVpp65 (pQE9 pp65n), for CMVpp65 with PK domain II mutation (pQE9 pp65mII), for CMVpp65 with PK domain VIII mutation (pQE9 pp65 mVIII), for CMVpp65 with PK domains II and VIII mutations (pQE9 pp65mII/VIII), and for CMVpp65 with carboxy-terminal truncation (pQE9 pp65 mTTH).

Accordingly, the present invention provides a cytomegalovirus pp65 protein which lacks protein kinase activity and which elicits a CTL response against cells infected with cytomegalovirus. Preferred embodiments of this protein contain the K436N mutation and in particular pcDNAintpp65mII. Further embodiments of the invention provide a DNA encoding such cytomegalovirus pp65 proteins.

The invention also provides vaccine compositions which comprise the cytomegalovirus pp65 proteins described above and the pharmaceutically acceptable carrier. Further embodiments of the invention provide a cellular vaccine composition which comprises antigen presenting cells that have been treated in vitro so as to present epitopes of a cytomegalovirus pp65 protein which lacks protein kinase activity and which elicits a CTL response against cells infected with cytomegalovirus and a pharmaceutically acceptable carrier. These DNA vaccines may further comprise an adjuvant. In addition, the invention provides a eukaryotic virus vector which comprises the DNAs described above.

The invention further provides a DNA vaccine composition which comprises a DNA which encodes a cytomegalovirus pp65 protein which lacks protein kinase activity and which elicits a CTL response against cells infected with cytomegalovirus and a pharmaceutical acceptable carrier.

The invention further provides a method of enhancing immunity to cytomegalovirus which comprises administering any of the vaccine compositions described above.

The invention further provides a diagnostic reagent for detecting the presence of active versus quiescent cytomegalovirus infections which comprises pp65mII transfected target antigen presenting cells.

DETAILED DESCRIPTION OF THE PREFERRED EMBODIMENTS

The present invention provides mutants of CMVpp65 which exhibit substantially no protein kinase activity but retain the immunological activity of the native sequence whereby they are capable of eliciting an antibody response and/or a CTL response against CMV in a suitable host. These mutants may differ in primary sequence from native CMVpp65 by one or more amino acid residues. One preferred embodiment comprises a mutant form of CMVpp65 that contains a point mutation that preserves native immunologically important epitopes but eliminates protein kinase activity.

The invention provides methods to augment the immune response of a host who is naive to CMV or to a patient latently infected with CMV and at risk for reactivation of CMV infection, wherein T cells are removed from a donor individual and treated in vitro with a mutant CMVpp65 DNA of the present invention that has been transfected into an HLA-matched antigen presenting cell. The resulting CMV-reactive CTL are infused into a recipient to provide protection from CMV disease.

The above methods also can be used to confer immunity against a CMV infection in a previously uninfected individual such as, for example, a woman of child-bearing years to prevent maternal-infant or maternal-fetus transmission of CMV. The methods can be used to vaccinate children to reduce the spread of CMV infection in, for example, day care centers. Vaccines may take any form known in the art, such as protein vaccines, DNA vaccines or recombinant live virus vaccines containing a DNA of this invention.

Adjuvants may form part of vaccine compositions. Any adjuvant known in the art which is suitable may be used. Examples include Freund's adjuvant, alum or any known adjuvant suitable for use with a protein vaccine. For in vivo use in humans, such adjuvants are not preferred. A DNA adjuvant may be used with a protein vaccine in humans, if desired. Genetic adjuvants may be used to enhance the effect of DNA immunization, for example genes encoding GM-CSF or IL-2. These genes may be inserted into the modified vector to enhance CTL activity. Carriers may be used with the vaccine compositions, including any pharmaceutically acceptable carrier known in the art. Exemplary carriers may include sterile water, saline solutions, liposomes or solutions containing cyclo-dextrin. Liposomes and cyclo-dextrin may be used to enhance uptake of the DNA by the antigen presenting cells.

Any suitable vector may be used in DNA vaccine compositions according to the invention. For example, pMG vector (Invitrogen) has been developed with two different promoters, one of which is the elongation factor 1α/HTLV hybrid. This is a strong promoter suitable for use with the DNA vaccines of this invention. The selection of hygromycin (bacteria) or Zeocin (mammalian) yields stable transfectants in two weeks.

The peptides of the mutant protein of the present invention may be administered to previously infected or uninfected patients, or in vitro to T cells, in the form of a protein vaccine or a polynucleotide (DNA-based) vaccine, or as a component of a recombinant viral vaccine. Suitable gene transfer vectors, such as a plasmid or an engineered viral vector that contains DNA encoding the CMVpp65 protein or a fragment thereof under the control of appropriate expression regulatory sequences may be administered to the patient or to T cells in culture for later administration to the patient. Therefore, the present invention provides a vaccinia, canarypox or other eukaryotic virus vector containing a DNA sequence encoding the immunologically active protein. The vector infects an antigen presenting cell which in turn presents antigen that will be recognized by CTL of patients having a latent (inactive) CMV infection.

A DNA vaccine permits direct and efficient expression of the protein of interest (pp65mII), that can be transfected easily in vitro or in vivo into an antigen presenting cell and trigger a cytotoxic T cell response. To accomplish this, a plasmid which has a promoter with high expression levels (e.g., the CMV IE promoter as used in pcDNAintpp65mII) is used. Preferably, the promoter also has an intron (e.g., intron A of the CMV IE gene as used in pcDNAintpp65mII) which stabilizes the expression of the DNA due to the presence of transcriptional enhancers. Finally, the preferred DNA vaccines have a polyadenylation termination sequence (e.g., bovine growth hormone poly A sequence as used in pcDNAintpp65mII). The vaccine sequence exemplified below (pcDNAintpp65mII) was derived from pcDNA3.1+ (Invitrogen), but for a safer vaccine, the ampicillin gene is preferably removed because it confers resistance to penicillin and is replaced with the kanamycin gene. In addition, the viral SV40 ori and pA preferably are removed to improve safety by diminishing the likelihood of integration into the host genome.

In regard to recombinant virus vectors, it is possible to use recombinant viruses that encode the CMV pp65mII gene to enhance the immunological response. Poxvirus recombinants such as recombinant vaccinia, modified vaccinia virus Ankara (MVA), and canarypox may be used for this type of recombinant viral vaccine production. Attenuated recombinant virus vaccine strains can be produced with multiple virus epitopes and with soluble cytokine factors that further augment the immune response. In vivo immunization of CMV seronegative subjects may be done with a DNAintpp65mII priming followed by a recombinant virus (e.g., vaccinia-pp65mII or MVApp65mII) boost to elicit specific CTL proliferation. The in vitro expansion of specific CTL may be done with matched-HLA stably transfected with pcDNAintpp65mII cell lines such as EBV-transformed B cells, such as LCL, and stimulators such as anti-CD3 antibody.

The invention also relates to diagnostic reagents for detection of the presence of active versus quiescent CMV infections. A human cell line, A293, stably transfected with pcDNAintpp65mII has been established and expresses the pp65mII protein. These cells can be used in a diagnostic assay to detect the presence of antibody to CMV in plasma and thus determine the CMV serology status by immunofluorescence or any suitable method. The specific CTL response can be assayed ex vivo using a cytokine-based assay, such as an IFN-γ elispot assay or FACS intracellular IFN-γ assay, whereby the T cells are stimulated in vitro for a period of time, with matched-HLA transfected/not transfected pp65mII LCL and the number of cytokine positive cells are determined. The IFN-γ positive CD8$^+$ cells are CTL that have been stimulated by the expression of the mutant peptide expressed in the LCL; the IFN-γ positive CD4+ cells are the T helper CD4 cells that have been stimulated to induce a TH1 pathway and generate more CTL.

Because the native PK activity of CMVpp65 may be harmful if expressed in healthy cells, vaccine methods using CMVpp65 which lacks this potentially harmful activity were created. To reduce or eliminate the PK activity of CMVpp65, expression plasmids were constructed in the pQE9 vector using site-specific mutations within the CMVpp65 protein, including mutations within the putative PK domains II and VIII at amino-acid locations 436 and 465. In addition, a complete carboxy-terminal truncation was created in pQE9pp65mTTH that represented a deletion of all the putative PK domains of CMVpp65 (aa398-552). A plasmid containing CMVpp150 served as an additional negative control to check for background PK activity of the expression system. See FIG. 1 and Example 1. The plasmids containing mutated CMVpp65 were compared to plasmid pQE9pp65n, containing the native CMVpp65, for kinase activity and protein expression. The bacterial expression system used here allowed PK activity to be tested without possible contamination of mammalian cellular kinases. Other suitable plasmids are well known in the art. Other suitable plasmids are continuously being developed as better expression vectors for in gene therapy or vaccine research. The mutant pp65 gene may be inserted in any of these vectors as seems fit. Therefore, any suitable plasmid is contemplated for use with this invention.

The choice of CMVpp65 sequences to mutagenize was based on available sequences that conformed to the conserved catalytic subdomains of known threonine/serine PKs (Hanks 1991) and yet did not overlap with known CMVpp65-specific CTL epitopes. CMVpp65 contains the conserved PK subdomains I, II, VIB, VIII, and XI. CTL epitopes overlap in domains I and in various parts of the CMVpp65 carboxy terminal sequence (50). Therefore, only domains II and VIII were selected for modification. Subdomain II contains lysine 436 that corresponds to the invariant lysine present in several PKs that is known to interact with ATP analogs that inhibit PK (27). In addition, mutating the lysine in domain II suppresses the PK activity of other typical protein kinases, such as the insulin receptor, the EGF receptor, and viral proteins, such as P130$^{gag\text{-}fps}$ of the Fujinami sarcoma virus and P37$^{mos}$ the transforming gene product of Moloney murine leukemia virus (5, 23, 24, 49). Subdomain VIII, although out of sequence order compared to VI b, contains the triplet Ala-Pro-Glu that lies near the PK catalytic site and that has been linked to a nearby autophosphorylation site (22). Therefore, lysine 436 and glutamic acid 465 were selected for mutagenesis.

Figure 2:
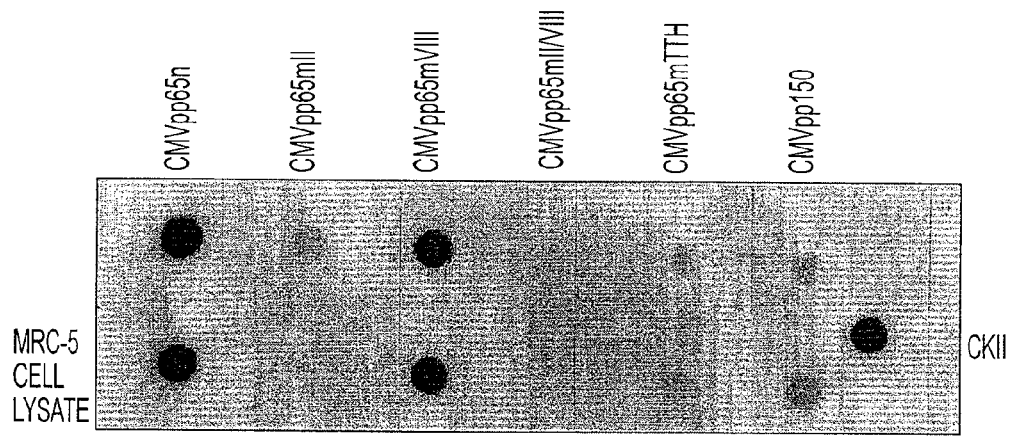
FIG. 2 provides a dot-blot protein kinase assay of CMVpp65 and its mutants immunoprecipitated from cell lysates of pQE9 transformed bacteria alone (upper row) or with MRC-5 cell lysates (lower row). CMVpp65 mTTH and CMVpp150 were used as negative controls.

The expression products of the plasmids containing the mutated sequences were first tested for protein kinase activity by dot blot using the exogenous substrate, casein. As shown in FIG. 2 (upper row), the (native protein) CMVpp65n possesses intrinsic protein kinase activity, resulting in phosphorylation of the exogenous substrate casein. The mutant CMVpp65mII, containing the K436N mutation, showed no detectable kinase activity. The mutant CMVpp65 mVIII showed approximately the same ability to phosphorylate casein as the native sequence, although there was a slight reduction in detectable phosphorylation. The combined mutant CMVpp65mII/VIII, with both K436N and E465K mutations demonstrated phosphorylation levels similar to the single mutant CMVpp65mII. The negative controls, CMVpp65 mTTH and CMVpp150, showed the level of background casein phosphorylation in the assay.

The CMVpp65mII mutant remained recognizable by a specific monoclonal antibody, as shown in western blot experiments. See FIG. 3. In addition, the CMVpp65mII protein localized to the nucleus of infected cells, as indicated by monoclonal antibody staining (data not shown), suggesting that the mutation did not significantly affect the normal trafficking of this protein. However, because the humoral immune response to CMVpp65 is not considered the most important element in the immune response to infection to viruses, it was more important to determine the effect of this mutation on CTL recognition and activation (cellular immunity). Therefore, cells infected with vaccinia-CMVpp65mII were tested for recognition as targets by a CTL clone derived from natural human infection.

Cells expressing native sequence (CMVpp65n), the mutated sequence (CMVpp65mII), wild type vaccinia virus (no sequence) or an HLA-mismatched control cells expressing the mutated sequence were all tested by chromium release assay for lysis by a human $CD8^+$ CTL clone specific for a CMVpp65 HLA A2 epitope. This $CD8^+$ CTL clone, 3.3F4 described in (10) the disclosures of which are hereby incorporated by reference, was obtained from a healthy CMV-seropositive human volunteer who had mounted a successful immune response to CMV, and is specifically reactive to HLA autologous targets expressing native CMVpp65. Cytolytic function against cells expressing the mutant was similar to that directed toward the native CMVpp65.

The mutant CMVpp65 proteins therefore are demonstrated to retain the immunological characteristics shown to be important in immune function in the human response to CMV infection, particularly cell-mediated immunity. The in vitro chromium release assays discussed above are well-recognized in the art to successfully correspond to in vivo function of the same cells. Therefore, HLA specific recognition of cells expressing the native protein by the human T lymphocyte clone 3.3F4 clearly demonstrates an equivalent cell-mediated immune response which is predictive of in vivo recognition, activation and cytolysis.

Further, data show CTL activation by CMVpp65 in a well-accepted animal model used for prediction of human vaccine responses. The HLA-A2.1 transgenic mouse model is accepted for use where no animal model is available to study the immunologic responses to a particular human virus. See Vitiello et al., J. Exp. Med. 173:1007, 1991. The cytotoxic response in HLA-A2.1 transgenic mice is shown to recognize the same epitopes as the ones presented in human cells in HCV (Wentworth et al., Int. Immunol., 1996), influenza (Man et al., Int. Immunol., 1995) or HIV (Ishioka et al., J. Immunol., 1999). The data therefore clearly demonstrate the feasibility of this approach for modifying the immune systems of human patients to protect both healthy and immunocompromised persons from CMV disease.

The following examples are provided as illustrations of methods of the invention and are not intended to be limiting in any way.

EXAMPLES

Example 1

DNA Constructions and Generation of Recombinant Vaccinia Virus

The CMVpp65 gene, cloned into the BamHI and EcoRI restriction sites of pBluescript II KS DNA (35) was used to create the constructs. CMV nucleotide coordinates were used as published (4). Mutations of the CMVpp65 DNA were made using a Quikchange™ site-directed mutagenesis kit (Stratagene, San Diego, Calif.) using the following pairs of mutagenic primers developed using the published PK domain characteristics (22, 28). 5' GCGGGCCGC AACCGCAAATCAGCATCC 3' and 5'GGATGCTGATTTGCGGTTGCGGCCCGC 3' (nt: 1270-1296; SEQ. ID NOS: 2 and 3) were used to mutate the indicated lysine into asparagine in the putative PK domain II (mII) of CMVpp65 (the K436N mutation). 5' GAGTCCACCGTCGCGCCCAAAGAGGACACCGACGAG 3' and 5' CTCGTCGGTGTCCTC TTTGGGGGCGACGGTGGACTC 3' (nt: 1345-1377; SEQ ID NOS: 4 and 5) were used to mutate the indicated glutamic acid into lysine in the putative PK domain VIII (mVIII) (the E465K mutation). The codon for the presumed functional amino acid K436 or E465 of CMVpp65 is shown underlined. Another mutant plasmid which contains both mII and MVIII (pp65mII/VIII) was also generated. The mutations were confirmed by DNA sequencing. A negative control lacking the putative CMVpp65 phosphokinase domain was created in pBluescript II KS (pp65 mTTH) by digesting the CMVpp65 gene with Tth111I and NSiI (New England Biolabs, Beverly, Mass.) to delete the nucleotides which encode CMVpp65 (amino acids 398-552). Overhanging sequences were removed with mung bean nuclease (New England Biolabs, Beverly, Mass.) and the ends re-ligated using T4 DNA ligase (Life Technologies, Inc., Gaithersburg, Md.).

To express the proteins in a bacterial system, the CMVpp65 DNA was removed from pBluescript using Sal I-Bam HI digestion and inserted downstream from the CMV promoter in the pQE9 vector (Qiagen, Valencia, Calif.). The pQE9 CMVpp65 expression plasmid was used to transform *E. coli* strain M15, which contains the repressor pREP4 plasmid, and the proteins were expressed following the manufacturer's protocol (Qiagen, Valencia, Calif.).

The mTTH modification of CMVpp65 was created to establish a kinase-deficient CMVpp65 control by inserting the Tth111I and NSiI truncations into the pQE9 plasmid. As shown in FIG. 1, the plasmid containing the native CMVpp65 was designated pQE9 pp65n, the K436N subdomain II mutant was pQE9 pp65mII, the E465K subdomain VIII mutant was pQE9 pp65 mVIII, the combined K436N/E465K mutant was pQE9 pp65mII/VIII, and the truncation control was pQE9 pp65 mTTH. pQE9 pp150 was used as a negative plasmid control. The CMVpp65 mutant sequences were subcloned into transfer vector pSC11 and then transfected using LIPOFECTAMINE (Life Technologies, Inc., Gaithersburg, Md.) into CV-1 cells that had been simultaneously infected with wild-type WR strain vaccinia virus using the method of Elroy-Stein and Moss (12). Recombinant virus was cloned and correct insertion was confirmed by PCR and DNA sequencing.

The efficiency of protein expression in the constructs was verified by western blot. The proteins were purified from cells transfected with the indicated pQE9 vector, separated using 12.5% SDS-PAGE, transferred to a nitrocellulose membrane and probed with mAb 28-103 specific for the detection of the pp65 protein (see Britt et al., J. Clin. Microbiol. 28:1229-1235, 1990), followed by ABC peroxidase staining using a VECTASTAIN ABC kit (Vector Laboratories, Inc., Burlingame, Calif.). All the proteins of the constructs bearing the intact carboxy-terminus of CMVpp65 were detected by the mAb, including the mutant CMVpp65. The level of expression was qualitatively similar in all constructs, suggesting that the mutations did not alter protein expression. In addition, mutation did not appear to significantly affect the immune recognition of the proteins.

Example 2

Immunoprecipitation of Recombinant CMVpp65

The CMVpp65 native and mutant proteins were expressed in the pQE9 bacterial system according to a Qiagenm™protocol. Cell pellets were extracted and subjected to immunoprecipitation as described by Michelson et al. (32) with modifications. Briefly, the bacterial pellets were frozen and thawed three times and incubated in lysis buffer (20 mN Tris/HCl pH 8.0, 300 mM NaCl, 10% glycerol, 2 mM EDTA, 0.5% Nonidet P-40) in the presence of protease inhibitor (5 μg/ml aprotinin and 5 μg/ml leupeptin) for 20 minutes at 40° C. The cell lysates were incubated with mouse IgG to remove nonspecific proteins, sonicated and then clarified by centrifugation at 15,000 x g for 5 minutes at 40° C. The CMVpp65 protein was immunoprecipitated with mAb28-103, specific for CMVpp65. Protein extract (200 μg) was mixed with 10 μl mAb28-103 unpurified ascites in 500 μl buffer A (10 mM TrisHCl, pH 7.4, 150 mN NaCl, 2 mN EDTA, 1% NP-40, with 5 μg/ml aprotinin and 5 μg/mi leupeptin (32)) and incubated at 4° C. for 90 minutes with agitation. When relevant, 100 pg MRC-5 cell lysate in 1% SDS was added to the mixture to check whether cellular kinases co-immunoprecipitated with the CMVpp65 protein. The immune complex was captured with 100 μl 50% protein A-Sepharose 4 Fast Flow beads (Amersham Pharmacia Biotech, Piscataway, NJ) co-incubated with the extract at 4° C. for 45 minutes and then washed three times by centrifugation with buffer A.

Example 3

Protein Kinase Assays

The immunoprecipitated native and mutant CMVpp65 proteins, still bound to the sepharose beads, were tested for protein kinase (PK) activity. pQE9 pplS0 was also processed in the same way, as a negative control. Casein kinase II (Promega, Madison, Wis.) enzyme was used as a positive control. Dot blot PK assays were performed according to the methods of Glover and Allis (20). Briefly, 100 μl samples to be assayed were immobilized on a nitrocellulose membrane (Hybond ECL, Amersham Pharmacia Biotech, Piscataway, N.J.) by vacuum filtration using a commercial dot blot manifold (Minifold, Schleicher & Schuell, Inc.). Dephosphorylated bovine casein (Sigma Chemical Co, St Louis, Mich.) (100 μl 1 mg/ml) was added to each well as substrate, followed by incubation at room temperature for 30 minutes with 100 μl reaction mix (25 mM Tris pH 8.5, 100 mM NaCl, 10 mM MgCl$_2$, 1 mM dithiothreitol, 0.1 μM [γ-$^{32}$P] ATP). At the end of the incubation, free radioactive ATP was removed by washing the membrane 10 times in PBS at 37° C. followed by incubation at 37° C. in a shaking bath containing 100 ml stripping solution (4 M guanidine hydrochloride, 1% SDS, 0.1% Tween-20, 0.5% β-mercaptoethanol) for 30 minutes, with a final wash in distilled water. Incorporation of [$^{32}$P]-ATP into protein was visualized by autoradiography. See FIG. 2. Mutant CMVpp65mII showed no kinase activity. To quantitate the amount of phosphokinase activity, serial dilutions of casein kinase II (Promega, Madison, Wis.) were assayed, and a standard curve was established using a PhosphorImager 445 SI (Molecular Dynamics, Sunnyvale, Calif.). The data were plotted and fitted to a linear curve from which CMVpp65-PK units were derived. One unit was defined as the amount of kinase needed to transfer 1 picomole of phosphate per minute at 37° C. using casein as substrate. Any values below 1.0 were considered negative.

Because native CMVpp65 undergoes autophosphorylation (3), the signals detected by PK assay using CMVpp65 are actually the combined results of both casein and CMVpp65 phosphorylation. To separate the two activities, a protein kinase assay was performed in solution according to the method described by Roby et al. (41) and then analyzed by SDS-PAGE. Immunoprecipitated recombinant proteins, including CMVpp65n, CMVpp65mII, CMVpp65 mVIII, CMVpp65mII/VIII, CMVpp65TTH and CMVpp150, were used in protein kinase reactions in solution and then separated by 12.5% SDS-PAGE. Typically, 50 μl sample and 50 μl casein substrate (1 mg/ml) were added to 100 μl of a twofold-concentrated reaction mix as described above. The reaction was incubated at 37° C. for 30 minutes and terminated by adding 20 μl 100 μM EDTA, and then heated in boiling water for 3 minutes, releasing the CMVpp65 protein from the Sepharose beads, and sedimented at 15,000×g for 1 minute. The phosphorylated proteins were precipitated with 10% trichloroacetic acid, washed in acetone, and resuspended in loading buffer to be analyzed by 12.5% SDS-PAGE. Phosphorylation of the separated proteins on the gel was visualized by autoradiography using X-OMAT™ AR5 film (Kodak, Rochester, N.Y.).

Since the immunoprecipitation step may copurify other kinases from human-derived cells as well as the specific CMVpp65 protein (16), the bacterial lysate was mixed with 100 μg of MRC-5 cell lysate. The results are shown in FIG. 2 (lower row). No increase in phosphate signal was detected in any of the samples, including the negative controls. The CMVpp65mII remained negative, suggesting that it did not bind cellular kinases. To quantify the phosphokinase activities among the various mutants, with or without the addition of human-derived cell lysate, serial dilutions of casein kinase II were used to standardize the activity as units per assay (standardization data not shown).

The CKII positive control had 10 U PK activity, the CMVpp65n had 10.3 U, CMVpp65 mVIII had 7.8 U, and CMVpp65mII, CMVpp65mII/VIII, CMVpp65 mTTH and CMVpp150 had no activity. When the MRC-5 cell lysate was added to the reaction, CMVpp65n and CMVpp65 mVIII had an activity equivalent to 10.4 U and 7.0 U respectively, whereas the other reactions remained negative. These results show that no detectable cellular kinases were coimmunoprecipitated from the system containing human-derived cell lysates using the mAb 28-103 to precipitate the CMVpp65 specific kinase.

Figure 3:
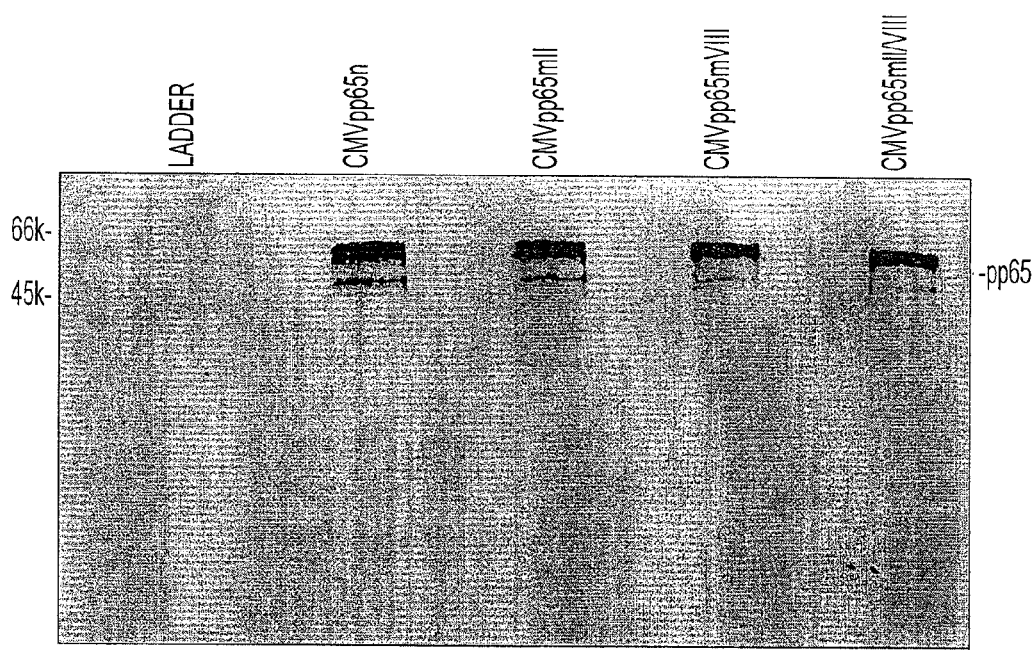
FIG. 3 is a western blot illustrating the expression of CMVpp65 and its mutants purified from cells transfected with the pQE9 expression system and probed with mAb 28-103.

The efficiency of the protein expression in the constructs was verified by western blot as shown in FIG. 3. Proteins expressed from the constructs bearing the intact carboxy-terminus of CMVpp65 are shown in this western blot. The CMVpp65 mutations are detected by mAb 28-103. The level of expression appears to be similar in all constructs, suggesting that the mutations did not alter protein expression. To perform the blot, a 1 ml culture of bacterial cells containing the expressed proteins in pQE9 were lysed in 100 μl lysis buffer, sonicated on ice three times for 30 seconds and sedimented at 15,000×g for 5 minutes. The protein concentration of the supernatants was measured and 100 μg protein was subjected to 12.5% SDS-PAGE, transferred to a nitrocellulose membrane and incubated with mAb 28-103 followed by staining with peroxidase. See FIG. 3.

Figure 4:
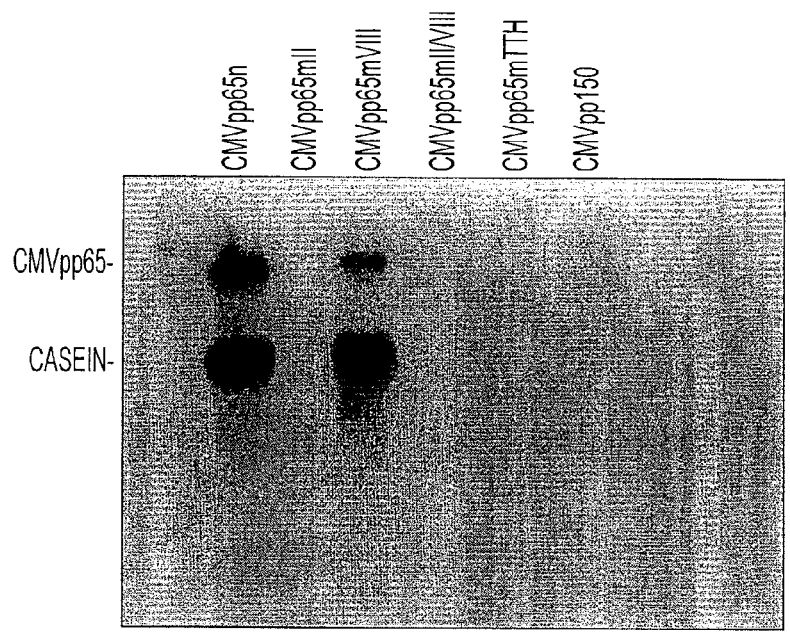
FIG. 4 shows a 12.5% polyacrylamide gel of the indicated autophosphorylated recombinant proteins separated from phosphorylated casein.

As shown in FIG. 4, CMVpp65 and casein were phosphorylated by CMVpp65n and CMVpp65 mVIII. CMVpp65mII, containing the substitution at K436N, showed not only complete loss of phosphorylation of casein but also absence of autophosphorylation. The same absence of autophosphorylation was observed with CMVpp65mII/VIII, as well as the negative controls CMVpp65 mTTH and CMVpp150.

Figure 5:
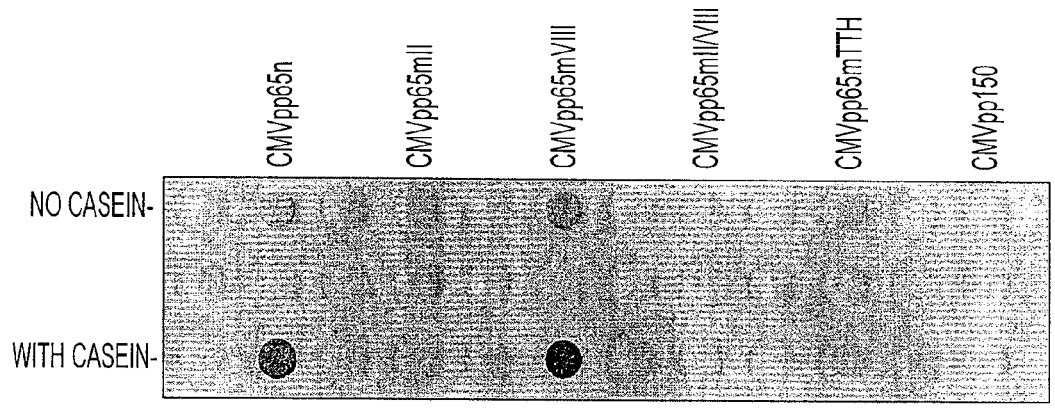
FIG. 5 is a membrane blot containing phosphorylated products, probed with antibodies specific to phosphorylated serine and threonine residues.

To further characterize which residues were phosphorylated, an SDS-PAGE membrane blot containing the phosphorylated products was incubated with specific monoclonal antibodies directed to the phosphorylated residues of serine and threonine. The PK assay was performed according to the same methods of the dot blot assay described above, except that unlabeled ATP (30 mM) was used in the sample reaction. Phosphorylation was detected by incubating the membrane with specific anti-phosphoserine or anti-phosphothreonine antibodies (2 μg/ml), (Sigma Chemical Co., St. Louis, Mo.) and revealed by immunoperoxidase staining using a VECTASTAIN ABC Kit (Vector Laboratories, Inc., Burlingame, Calif.) (40). The results (FIG. 5) showed that autophosphorylation (without casein as substrate) and casein phosphorylation were revealed using anti-phosphothreonine antibody only with the CMVpp65n and CMVpp65 mVIII reactions, but not with CMVpp65mII and CMVpp65m II/VIII or with the negative control CMVpp65 mTTH and CMVpp150. No serine phosphorylation was detected in any of the immunoprecipitated CMVpp65 protein (data not shown). See FIG. 5.

Example 4

Chromium Release Assay

To investigate whether the mutation of the PK domains in CMVpp65 interferes with epitope presentation on a target cell surface for recognition by CTL, chromium release assays were performed. A human CD8+ CTL clone 3.3F4, with specificity for CMVpp65 HLA A2 epitope (10) was used as the effector in a chromium release assay using HLA-type (LCL-A2) matched or mismatched (LCL-All) EBV-transformed B lymphocyte targets. All target cells were infected with vac-pp65n, vac-pp65mII or wild-type vaccinia virus (vac-wt) overnight at MOI=5, then incubated for four hours with 200 μCi $^{51}$Cr (ICN Pharmaceuticals Inc., Costa Mesa, Calif.). The MHC-mismatched control LCL-All also was infected with vac-pp65mII. The cells were assayed using the methods of McLaughlin-Taylor et al. (30). Spontaneous release (without effector) and maximum release (lysed in 2% SDS) of radioactivity were determined for each target. Specific cytotoxicity was expressed as (effector cpm−spontaneous release cpm)/(maximum release cpm−spontaneous release cpm)×100.

Figure 6:
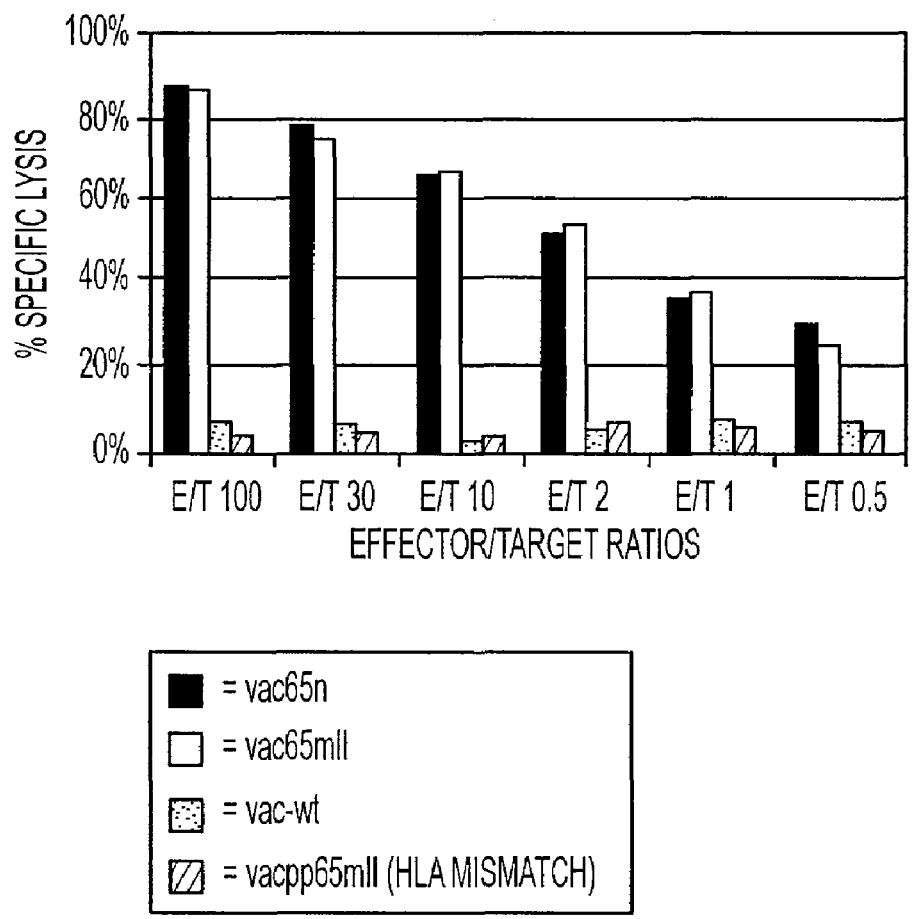
FIG. 6 is a bar graph showing the results of a chromium release assay using human T lymphocyte clone 3.3F4 effector cells and HLA-matched or -mismatched target cells infected with recombinant vaccinia virus.

As shown in FIG. 6, clone 3.3F4 recognized cells presenting the CMVpp65 mII epitope as efficiently as cells expressing the CMVpp65n (native) epitope. There was no significant difference in cytolytic effect at any of the various effector-to-target (E:T) ratios. This suggests that the point mutation of the invariant lysine K436N, which eliminates PK activity, does not negatively affect the HLA-restricted presentation of CMVpp65 CTL epitope.

Example 5

CMVpp65 DNA Immunization of Transgenic HLA A*0201 Mice

Transgenic HLA A*0201 mice were immunized with CMVpp65 DNA to test for CTL activity in response to the immunogen. The transgenic mice have been described previously by Benmohammed et al., Hum. Immunol. 61:764-778, 2000 and Vitiello et al., J. Exp. Med. 173:1007, 1991. The known CMV epitope, NLVPMVATV (SEQ ID NO: 6; Peninsula Laboratories, Inc. San Carlos, CA; 95% pure) was used in a specific chromium release assay to demonstrate the efficacy of the DNA vaccine administered to the mice. The mice express human HLA antigens, therefore this mouse model permits the study of the immunologic response to human CMV as presented in the context of a normal human HLA molecule and to evaluate the protection a vaccine will elicit in humans. The specific epitope of SEQ ID NO: 6 is known to elicit human CD8+T cell activity in HLA A*0201 CMV-seropositive individuals. in the context of a normal human HLA molecule and to evaluate the protection a vaccine will elicit in humans. The specific epitope of SEQ ID NO: 6 is known to elicit human CD8+ T cell activity in HLA A*0201 CMV-seropositve individuals.

The CMVpp65 gene was inserted into the pBluescriptII KS+ vector and was modified as follows. The CMV intron A of the immediate-early gene (823 bp) was inserted in front of the pp65 gene at the Spe1/BamH1 site using PCR with the following primers:

```
Forward:
5'-GAATTCACTAGTGTAAGTACCGCC-3'.        (SEQ ID NO: 7)
        EcoR1  Spe1

Reverse:
5'-GACTGGATCCCTGCAGAAAAGACCC-3'.       (SEQ. ID NO: 8)
        BamH1
```

Figure 7:
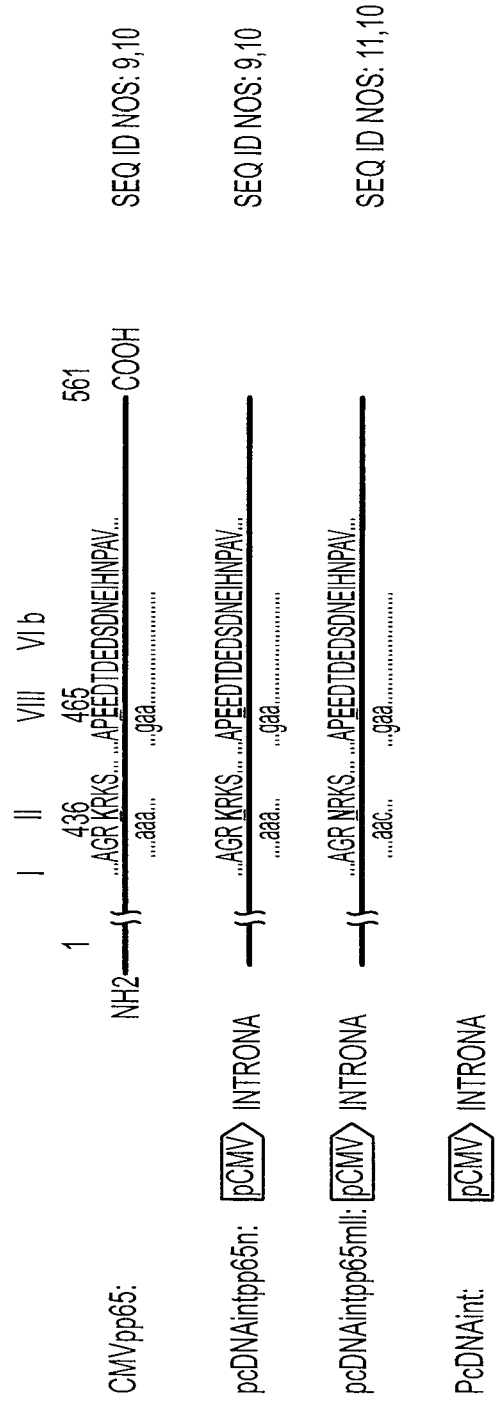
FIG. 7 is a schematic illustration of CMVpp65, pcDNAintpp65n, pcDNAintpp65mII and pcDNAint.

The intronA/CMVpp65 gene, still in pBluescript (see FIG. 7), was mutagenized as described in Example 1 using the Quickchange™ site-directed mutagenesis kit (Strategene, San Diego, Calif.). The intronA/CMVpp65 mutant II gene (pcDNAintpp65mII), the expression product of which exhibits no phosphokinase activity, was removed from pBluescript with the Spe1 and EcoR1 site of the pcDNA 3.1+ vector (Invitrogen, San Diego, Calif.). The control plasmids, including the intronA/CMVpp65 native (pcDNAintpp65n) and the intron A alone (pcDNAint), were inserted in the pcDNA3.1+ vector as well. All plasmids' DNA were transformed in DH5α competent cells, grown in terrific broth (Gibco-BRL Life technologies, Grand Island, N.Y.) and isolated using the Qiagen Maxi kit (Qiagen, Valencia, Calif.).

The intronA/CMVpp65n and intronA/CMVpp65mII DNA were removed from pBluescript, inserted into the pSC11 vector at the SpeI and KpnI site, and transfected into CV1 cells as described above in Example 1. The CV1 cells were simultaneously infected with WR strain vaccinia and the recombinant plasmid and were plaque purified three times to ensure clonality and purity. To titer the vaccinia virus in the ovaries, CV1 cells were plated at a density of $1.25\times10^5$ cells per well in a 24 well plate. The ovaries were collected, dissected free of fat tissue, weighed and frozen at −80° C. until ready for processing. They were homogenized with a TEFLON homogenizer on ice, sonicated three times for 30 seconds, resuspended in 100 µl of medium and diluted serially. An aliquot was added to the CV-1 cells, incubated overnight and stained with crystal violet the next day.

Transgenic HLA-A2.1 mice were constructed by microinjection of a chimeric molecule containing the α2 domains of the HLA-A*0201 gene and the α3 domain of murine H-2 Kb into fertilized eggs from C57Bl/6 mice as described previously (Hogan, et al., 1986. Manipulating the Mouse Embryo-Laboratory Manual Cold Spring Harbor Laboratory. Cold Spring Harbor, N.Y.; Vitiello et al., J. Exp. Med. 173:1007, 1991). The HLA-A*0201 expression was verified by FACS using mAb BB7.2, Parham et al., Hum. Immunol. 3:277-99, 1981; Benmohammed et al., Hum. Immunol. 61: 764-779, 2000, and by PCR according to a modified protocol described by Krausa et al., Tissue Antigens 45:223-231, 1995. The transgenic mice were called TgA2/$K^b$ for the chimeric MHC molecule.

Six to eight week old TgA2 $K^b$ mice were inoculated intra-muscularly every 4 weeks with 50 µg Qiagen column purified DNA in 50 µl sterile PBS in each thigh. The mice were immunized with pcDNAintpp65n, pcDNAintpp65mII and pcDNAint as control plasmid. The spleens were collected 4 weeks after the last immunization. When applicable, the mice were challenged on day 7 after the last inoculation, IP, with $5\times10^6$ pfu of recombinant vaccinia expressing pp65n and the ovaries were collected 5 days later to titer vaccinia. The spleens were collected as well to check for the presence of specific CMVpp65 CTL.

Blood samples were collected prior to each injection during the immunization process and the sera isolated and frozen at −20° C. The sera were diluted at 1/50 and 1/100 and incubated with MRC-5 cells previously infected with Toledo CMV strain for 3 days. The presence of the pp65 protein was revealed with a biotinylated antimouse IgG and immunoperoxidase labeling (Vector Laboratories, Inc., Burlingame, Calif.). When the sera were positive for pp65 Ab, they were subjected to an ELISA for quantitation.

Example 6

Detection of Specific CTL Activation Elicited by CMVpp65 DNA Vaccine

Three days before the harvest of effector cells from immunized TgA2 $K^b$ mice, blasts cells were prepared from syngeneic spleen cells (1 spleen for 3 immunized mice) and cultured at a concentration of $1\times10^6$ cells/ml in complete RPMI (10% heat-inactivated FBS, 50 units/ml Pen/Strep, 10 mM Hepes, 2 mM L-glutamine, $5\times10^{-5}$ M β-mercaptoethanol) and stimulated with 25 µg/ml LPS (Sigma, St Louis, Mo.) and 7 µg/ml dextran sulfate (Sigma, St Louis, Mo.). The cells were subjected to in vitro stimulation (IVS) as follows. Stimulated blast cells (targets), resuspended at a concentration of $25\times10^6$ cells/0.2 ml serum-free RPMI with 100 µM CMVpp65peptide$_{495}$ (SEQ ID NO:6) and 3 µg/ml of β2-microglobulin, were incubated at 37° C. for 4 hours with regular mixing to load the targets with peptide. The cells then were irradiated at 3000 RADS using a Isomedix Model 19 Gammator (Nuclear Canada, Parsippany, N.J.) and plated in a 24 well plate ($1\times10^6$ blasts per well) in complete RPMI supplemented with 10% rat T-stim culture supplement (Becton-Dickinson, Franklin Lakes, N.J.). Each well also contained $3\times10^6$ immunized spleen cells. A second IVS procedure was done 7 days later using the same protocol.

T2 cells (ATCC CRL-1992), LCL-A2 cells (human EBV transformed cell), EL4A2 cells (mouse H-2b cell stably transfected with the A2 gene) presenting the HLA-A*0201 allele and LCL-A3 cells (control HLA cell line) were used as targets. For chromium release assay (HLA-specific, antigen-specific cytolysis assay), the target cells were incubated with 200 µCi$^{51}$Cr with or without peptide (100 µM) and 12-microglobulin (3 µg/ml) for 1 hour at 37° C. They were washed and mixed at a effector:target (E/T) ratio of 100:1 to 10:1 in a 96-well bottom plate with effector cells (immunized spleen cells). The effectors and targets were co-incubated for 4 hours and an aliquot was counted using a Topcount TM counter (Packard Instrument Co, Downers Grove, IL.). Specific CTL clones (e.g. 19M3) were maintained in culture by weekly stimulation with peptide loaded blasts in complete RPMI with 10% rat stim or 20 units/ml of rhIL-2.

Figure 8A:
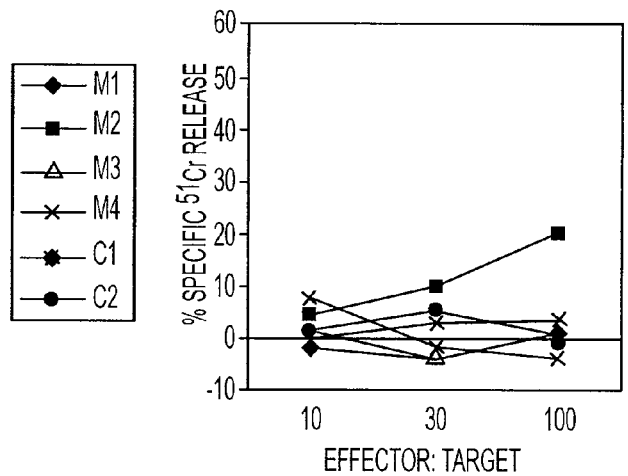
FIG. 8 presents data showing the percent specific $^{51}$Cr release from peptide-loaded T2 cells by spleen cells from CMVpp65 immunized mice after one in vitro stimulations (8A), two in vitro stimulations (8B) and from HLA-mismatched target cells (8C).
Figure 8B:
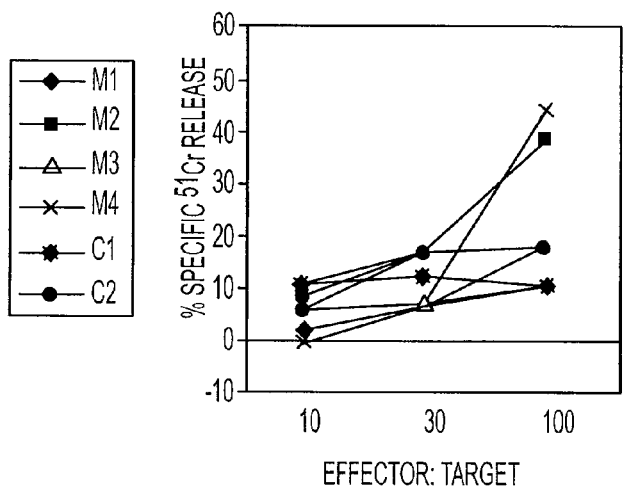
Figure 8C:
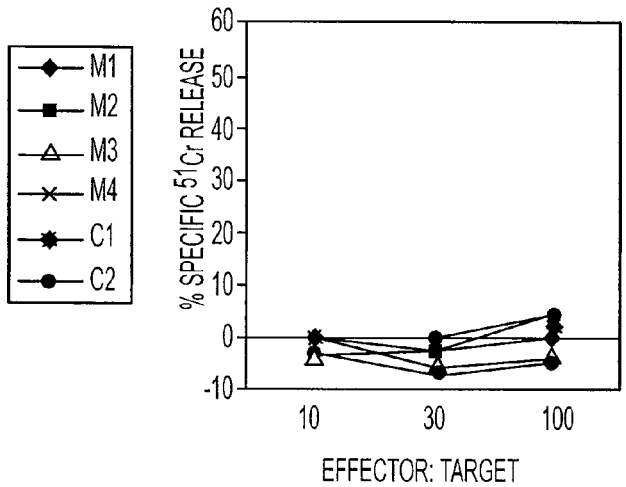

Four mice were immunized with pcDNAintpp65n and two mice with pcDNAint (controls). One out of four mice generated specific CTL which recognized and lysed peptide pp65$_{495}$ loaded T2 cells after one in vitro stimulation (20% lysis), and two after a second in vitro stimulation (39% and 44% lysis). The effector cells from mice immunized with control DNA did not lyse the target cells, showing that the assay was specific. The other control HLA-mismatch LCLA3 target cells were not lysed by either responsive CTL cells M2 and M4. The results show that construct, pcDNAintpp65n, which expresses the native gene of CMVpp65, elicits CTL activity in the transgenic mouse model. More importantly, the CTL generated specifically recognize the minimal cytotoxic epitope of pp65 for the HLAA*0201, NLVPMVATV (SEQ. ID NO:6), presented by the human cell line T2. See FIG. 8 for results.

Example 7

Kinase Deficient CMVpp65 DNA Vaccine Elicits Specific Cellular Immunity

Figure 9:
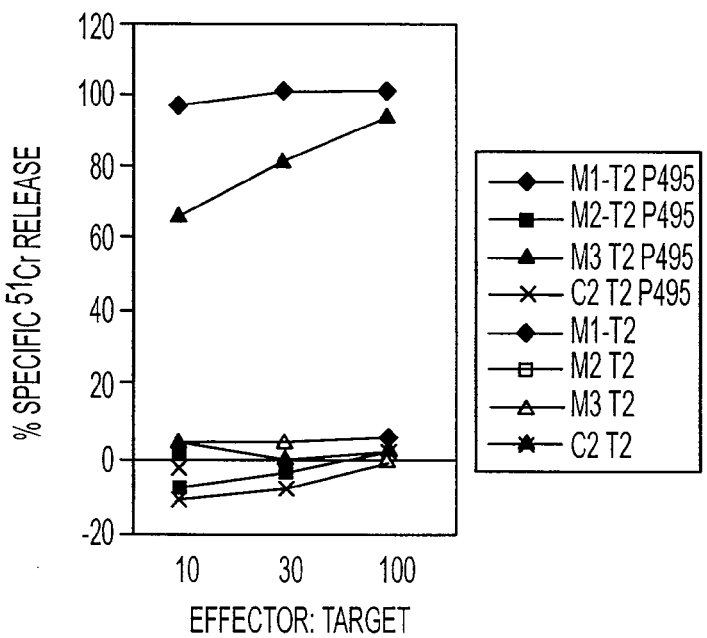
FIG. 9 shows the same results as FIG. 8A except mice were immunized with a kinase-deficient CMVpp65 DNA vaccine.

The methods of Example 6 were repeated, except that the mice were vaccinated with pcDNApp65mII gene inserted in the same mammalian expression vector as pcDNApp65n. Two out of 3 mice responded to pcDNApp65mII DNA immunization with almost 90% specific lysis of the target T2 cell loaded with the epitope of SEQ ID NO:6. See FIG. 9. The mutated CMV protein therefore is at least equivalent to the native sequence in its ability to elicit a CTL response.

Example 8

Figure 10:
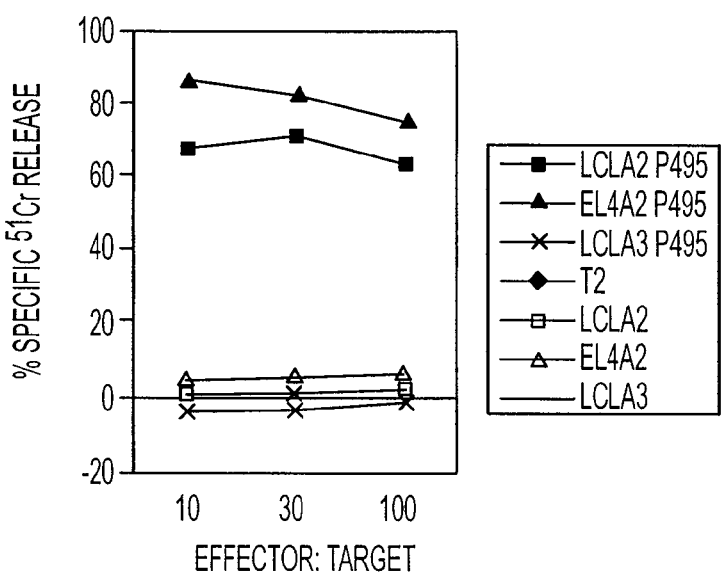
FIG. 10 presents chromium release assay results showing the ability of a CTL clone to lyse the indicated different target cell lines, each loaded with a CMV peptide.

A CTL Clone Generated from Mutant CMVpp65 Immunization Specifically Recognizes Only HLA Compatible Targets A CTL clone (19M3) generated by the mutant pp65 immunization and weekly stimulation with SEQ ID NO:6 loaded blasts was grown in culture and used to lyse the following target cell lines: T2, LCLA2, EL4A2 and LCLA3 (HLA mismatch). Only the HLA A*0201 expressing cells were lysed. See FIG. 10. These results demonstrate that the mutant CMVpp65 protein elicits specific CTL activity and performs the functions necessary for successful vaccination.

Two CTL clones were not able to lyse HCMV-infected fibroblasts, however fibroblasts infected with the Towne strain of CMV at an MOI of 5 were lysed at 30% and peptide loaded T2 cells at 85% by the CTL clones. See FIG. 10 and Table I. The serum from immunized mice were tested for specific antibody response to the pp65 protein by immunohistochemistry on CMV-infected MRC-5 cells (infected for 3 days at MOI: 02). The mice in each immunization group, pp65n or pp65mII, which developed cytolytic activity to the pp65 protein, responded with antibody production.

Example 9

Elispot Assay for CMV Diagnosis

Sterile microtiter plates are coated with 100 μl per well rat anti-mouse IFN-γ (2 μg/ml) in 50 mM sterile filtered carbonate buffer, pH 9.6 (21 μl/10.5 ml) with overnight incubation. The plates then are washed twice with RPMIc and blocked for 1-3 hours. The medium is replaced and 2× or 3× serial dilutions of effector cells (from $1 \times 10^6$ to $1.25 \times 10^5$ in 100 μl) irradiated feeder/target cells ($2.5 \times 10^5$ cells plus/minus peptide or transfected with pp65mII in 50 μl or $5 \times 10^6$ c/ml). Stimulation factors (conA, peptides, pp65) are added, plus rat stim. Cell lines such as T2 (loaded or not loaded with peptides) also may be used. After 8-24 hours incubation, the plate is washed with $DIH_2O$ cycle P03M8 to remove the cells, then with 1× PBS plus 0.05% Tween-20 (PBST) with cycle P03M8 and blotted. Biotinylated anti-IFN-γ (100 μl/well; 1.25 μg/ml in PBST; Pharmingen, San Diego) was incubated in the wells overnight at 4° C. The bound antibody is detected with an alkaline phosphatase streptavidin according to known methods.

(14) Forman et al., Transplant. Proc., 1:507-9, 1985.
(15) Gallina et al., J. Virol., 73: 1468-78, 1999.
(16) Gallina et al., J. Gen. Virol. 77:1151-7, 1996.
(17) Garcea et al., J. Virol. 54:311-6, 1985.
(18) Gilbert et al., Nature 383: 720-2, 1996.
(19) Glover et al., San Diego, Calif.: Academic Press, Inc.; pp. 85-90, 1991.
(20) Hanks et al., Methods Enzymol., 200:38-62, 1991.
(21) Hanks et al., Science, 241:42-52, 1988.
(22) Hannink et al., Biochemistry, 82:7894-98, 1985.
(23) Honegger et al., Cell, 51: 199-209, 1987.
(24) Hunter et al., Ann. Rev. Biochem., 54:897-930, 1985.
(25) Jacobson et al., AIDS, 12:S157-63, 1998.
(26) Kamps et al., Mol. Cell. Biol., 6:751-7, 1986.
(27) Leader, Nature, 333:308, 1988.
(28) McGeoch et al., Nucleic Acid. Res., 14: 1765-77, 1986.
(29) McLaughlin-Taylor et al., J. Med. Virol., 43:103-10, 1994.
(30) Michelson et al., Eur. J. Biochem., 149:393-9, 1985.
(31) Michelson et al., Virology 134:259-68, 1984.
(32) Ohlin et al., Clin. Diagn. Lab. Immunol., 2:325-9, 1985.
(33) Pande et al., Scan. J. Inf. Dis., 99:117-20, 1995.
(34) Pande et al., Virology, 178:6-14, 1990.
(35) Paoletti et al., J. Virol., 10:417-24, 1972.
(36) Pass, Infect. Agents Dis., 5:240-4, 1996.
(37) Raynor, Semin. Perinatol, 17:394-402, 1993.
(38) Riddell et al., J. Immunol., 146:2795-804, 1991.
(39) Rijksen et al., Academic Press, Inc., pp. 98-107, 1991.

TABLE I

Cytolytic Response to CMVpp65 DNA Immunization with a Vaccinia Challenge (recvacpp65n).

| | | Ex vivo Response | | | Response after One In Vitro Stimulation | | | Response after Two In Vitro Stimulations | | | Vaccinia Titer per Ovary |
|---|---|---|---|---|---|---|---|---|---|---|---|
| | E/T Ratio | 10 | 30 | 100 | 10 | 30 | 100 | 10 | 100 | 100 | |
| DNApp65mII | M2 | 1.8 | 4 | 9.2 | 7.8 | 15.2 | 45.6 | ND | ND | ND | $3.4 \times 10^4$ |
| | M4 | 1.5 | 1.6 | 4.4 | 0.2 | 8.3 | 16.7 | ND | ND | ND | $3.9 \times 10^4$ |
| | M4(2) | 1.1 | 0.3 | 3.4 | 3.97 | 1.81 | 13.24 | 22 | 51.2 | 81.7 | 5 |
| | M3 | −1.3 | −3.7 | −3.4 | 0.2 | −2.2 | −1.1 | ND | ND | ND | $9.5 \times 10^4$ |
| | M3(2) | 1.9 | 0.3 | 0.4 | −3.9 | 3.31 | 0.12 | 1.3 | 8.9 | 24 | $4 \times 10^6$ |
| | M1 | −2.1 | −1.3 | 2.9 | −1.8 | −0.6 | 1.9 | ND | ND | ND | $1.25 \times 10^5$ |
| DNApp65n | M3 | −1.4 | 0.2 | −2.7 | 2.3 | 2.83 | 18.17 | 8.49 | 12.11 | 28.09 | $2.75 \times 10^4$ |
| | M1 | 3.2 | 0 | 4.3 | −0.7 | −1.43 | −2.2 | −2.63 | 0.59 | 5.92 | $6 \times 10^4$ |
| | M2 | −3 | −1.1 | 1.2 | −1.6 | 0.47 | −4.9 | 5.46 | 6.38 | 3.55 | $1.4 \times 10^5$ |
| | M4 | −2.2 | −2.4 | −2.6 | 0.24 | −3.2 | −2.6 | 0.59 | −1.97 | 0.53 | 5 |
| pcDNAint | C1 | −0.6 | −1 | 1.9 | −2.7 | −4.14 | −2.35 | −6.12 | −2.57 | −1.78 | $2 \times 10^4$ |
| | C2 | −1.2 | −0.7 | −1.7 | −2.02 | −0.45 | −0.33 | 1.64 | 2.96 | 12.11 | $2.3 \times 10^4$ |

REFERENCES (1) Boppana et al., J. Virol., 222:293-6, 1996.
(2) Borysiewicz et al., J. Exp. Med. 168:919, 1988.
(3) Britt et al., J. Virol., 59:185-8, 1986.
(4) Chee et al., CTMI, 154: 125-69, 1990.
(5) Chou et al., J. Biol. Chem., 262:1842-47, 1997.
(6) Churchill et al., J. Infect. Dis., 155:501-9, 1987.
(7) Cohen, Eur. J. Biochem., 151:439-48, 1985.
(8) Dal Monte et al., J. Virol., 70:2086-94, 1996.
(9) Demmler, Semin. Pediatr. Neurol., 1:36-42, 1994.
(10) Diamond et al., Blood, 90(5):1751-67, 1997.
(11) Edelman et al., Ann. Rev. Biochem., 56:567-613, 1987.
(12) Elroy-Stein et al., New York, N.Y.: Greene Publishing; p. 16-63, 1991.
(13) Endresz et al., Vaccine 17:50-8, 1999.
(40) Roby et al., J. Virol., 59:714-27, 1986.
(41) Sanchez et al., J. Virol., 72:3321-9, 1998.
(42) Schmolke et al., J. Virol., 69:1071-8, 1995.
(43) Solache et al., J. of Immunol., 163:5512-8, 1999.
(44) Somogyi et al., Virology, 174(1):276-85, 1990.
(45) Stein et al., Bioessays, 17:537-43, 1995.
(46) Strand et al., Nature New Biology, 233:137-40, 1971.
(47) Tegge et al., Human Press, Inc., 1997.
(48) Weinmaster et al., EMBO J., 5:69-76, 1996.
(49) Wills et al., J. Virol., 70:7569-79, 1996.
(50) Wilson et al., Virology, 143:526-35, 1995.
(51) Witt et al., Virology, 107:34-49, 1980.
(52) Zaia, Blackwell Science, pp. 560-583, 1999.

The invention claimed is:

1. A vaccine composition which comprises a mutant cytomegalovirus pp65 protein that lacks protein kinase activity and that when administered to a mammal elicits a CTL immune response against cells infected with cytomegalovirus, wherein said cytomegalovirus pp65 protein contains a site-specific mutation at amino acid 436 or at both amino acid 436 and amino acid 465.

2. A vaccine composition of claim 1 wherein said cytomegalovirus pp65 protein contains the K436N mutation.

3. A vaccine composition of claim 1 which further comprises an adjuvant.

4. A method of enhancing immunity to cytomegalovirus which comprises administering a vaccine composition of claim 1.

5. A vaccine composition which comprises a mammalian expression vector which contains a nucleic acid that encodes a mutant cytomegalovirus pp65 protein that lacks protein kinase activity and that when administered to a mammal elicits a CTL immune response against cells infected with cytomegalovirus, wherein said cytomegalovirus pp65 protein contains a site-specific mutation at amino acid 436 or at both amino acid 436 and amino acid 465.

6. A vaccine composition of claim 5 wherein said pp65 protein contains the K436N mutation.

7. A vaccine composition of claim 5 wherein said nucleic acid encodes CMV pp65mII.

* * * * *

UNITED STATES PATENT AND TRADEMARK OFFICE
CERTIFICATE OF CORRECTION

PATENT NO.       : 7,387,782 B2
APPLICATION NO.  : 11/206162
DATED            : June 17, 2008
INVENTOR(S)      : John A. Zaia et al.

It is certified that error appears in the above-identified patent and that said Letters Patent is hereby corrected as shown below:

Title Page, Item (56) Ref. Cited:

In "Other Publications"

Page 2, Col. 2, line 6, Plotkin reference: "et a.," should be
-- et al., --

Page 2, Col. 2, line 62, Benmohamed reference: "A★0201/DR1"
should be -- A*0201/DR1 --

Page 3, Col. 1, line 18, Solache reference: "A★0201" should
be -- A*0201/DR1 --

Col. 3, line 17: "pQE9 pp65 mVIII" should be
-- pQE9pp65mVIII --

Col. 3, line 18: "pQE9 pp65mII/VIII" should be
-- pQE9pp65mII/VIII --

Col. 3, line 19: "pQE9 pp65 mTTH" should be
-- pQE9pp65mTTH --

Col. 3, line 23: "CMVpp65 mTTH" should be
-- CMVpp65mTTH --

Col. 5, line 49: "CMV pp65mII" should be -- CMVpp65mII --

Col. 7, line 4: "CMVpp65 mVIII" should be -- CMVpp65mVII --

UNITED STATES PATENT AND TRADEMARK OFFICE
CERTIFICATE OF CORRECTION

PATENT NO. : 7,387,782 B2
APPLICATION NO. : 11/206162
DATED : June 17, 2008
INVENTOR(S) : John A. Zaia et al.

It is certified that error appears in the above-identified patent and that said Letters Patent is hereby corrected as shown below:

Col. 7, line 10: "CMVpp65 mTTH" should be
-- CMVpp65mTTH --

Col. 8, line 37: "pp65 mTTH" should be -- pp65mTTH --

Col. 8, line 57: "pQE9 pp65n" should be -- pQE9pp65n --

Col. 8, line 58: "pQE9 pp65mII" should be -- pQE9pp65mII --

Col. 8, line 59: "pQE9 pp65 mVIII" should be
-- pQE9pp65mVIII --

Col. 8, line 60: "pQE9 pp65mII/VIII" should be
-- pQE9pp65mII/VIII --

Col. 8, line 61: "pQE9 pp65 mTTH" should be
-- pQE9pp65mTTH --

Col. 8, line 61: "pQE9 pp150" should be -- pQE9pp150 --

Col. 9, line 32: "40° C." should be -- 4° C. --

Col. 9, line 35: "40° C." should be -- 4° C. --

Col. 9, line 38: "TrisHCl" should be -- Tris/HCl --

Col. 9, line 38: "150 mN" should be -- 150 mM --

Col. 9, line 39: "2 mN" should be -- 2 mM --

UNITED STATES PATENT AND TRADEMARK OFFICE
CERTIFICATE OF CORRECTION

PATENT NO. : 7,387,782 B2
APPLICATION NO. : 11/206162
DATED : June 17, 2008
INVENTOR(S) : John A. Zaia et al.

It is certified that error appears in the above-identified patent and that said Letters Patent is hereby corrected as shown below:

Col. 9, line 40: "5 μg/mi" should be -- 5μg/ml --

Col. 9, line 56: "pQE9 pplS0" should be -- pQE9pp150 --

Col. 9, line 66: "Mich." should be -- Missouri --

Col. 10, line 29: "CMVpp65 mVIII" should be
    -- CMVpp65mVIII --

Col. 10, line 58: "CMVpp65 mVIII" should be
    -- CMVpp65mVIII --

Col. 10, line 59: "CMVpp65 mTTH" should be
    -- CMVpp65mTTH --

Col. 11, line 17: "CMVpp65 mVIII" should be
    -- CMVpp65mVIII --

Col. 11, line 22: "CMVpp65 mTTH" should be
    -- CMVpp65mTTH --

Col. 11, line 40: "CMVpp65 mVIII" should be
    -- CMVpp65mVIII --

Col. 11, line 42: "CMVpp65 mTTH" should be
    -- CMVpp65mTTH --

UNITED STATES PATENT AND TRADEMARK OFFICE
CERTIFICATE OF CORRECTION

PATENT NO. : 7,387,782 B2
APPLICATION NO. : 11/206162
DATED : June 17, 2008
INVENTOR(S) : John A. Zaia et al.

It is certified that error appears in the above-identified patent and that said Letters Patent is hereby corrected as shown below:

Col. 12, lines 32-36: delete second instance of "in the context of a normal human HLA molecule and to evaluate the protection a vaccine will elicit in humans. The specific epitope of SEQ ID NO: 6 is known to elicit human $CD8^+$ T cell activity in HLA A*0201 CMV seropositive individuals."

Col. 13, line 17: "Kb" should be -- $K^b$ --

Col. 13, line 27: "TgA2 $K^b$" should be -- $TgA2K^b$ --

Col. 13, line 54: "TgA2 $K^b$" should be -- $TgA2K^b$ --

Col. 14, line 13: "12-microglobulin" should be -- β2-microglobulin --

Signed and Sealed this

Sixteenth Day of December, 2008

JON W. DUDAS
*Director of the United States Patent and Trademark Office*